United States Patent
Prieels et al.

(10) Patent No.: US 8,859,980 B2
(45) Date of Patent: Oct. 14, 2014

(54) DEVICE AND METHOD FOR ONLINE QUALITY ASSURANCE IN HADRON THERAPY

(75) Inventors: Damien Prieels, Villers-la-ville (BE); Victor Breev, Louvain-la-neuve (BE)

(73) Assignee: Ion Beam Applications S.A., Louvain-la-neuve (BE)

( * ) Notice: Subject to any disclaimer, the term of this patent is extended or adjusted under 35 U.S.C. 154(b) by 1323 days.

(21) Appl. No.: 12/594,156

(22) PCT Filed: Mar. 29, 2008

(86) PCT No.: PCT/EP2008/053774
§ 371 (c)(1),
(2), (4) Date: Jan. 21, 2010

(87) PCT Pub. No.: WO2008/119777
PCT Pub. Date: Oct. 9, 2008

(65) Prior Publication Data
US 2010/0108901 A1 May 6, 2010

(30) Foreign Application Priority Data
Mar. 30, 2007 (EP) ..................... 07105403

(51) Int. Cl.
*G01T 1/18* (2006.01)
*H01J 47/00* (2006.01)
*A61N 5/10* (2006.01)
*H01J 47/02* (2006.01)

(52) U.S. Cl.
CPC ............... *H01J 47/02* (2013.01); *A61N 5/1075* (2013.01); *A61N 2005/1076* (2013.01); *A61N 2005/1087* (2013.01)
USPC .......................................... 250/374; 250/389

(58) Field of Classification Search
USPC ............... 250/370.07, 374, 382, 389, 390.01, 250/390.03
See application file for complete search history.

(56) References Cited

U.S. PATENT DOCUMENTS

| | | |
|---|---|---|
| 4,131,799 A | 12/1978 | Stieber |
| 5,041,730 A | 8/1991 | Attix |

(Continued)

FOREIGN PATENT DOCUMENTS

| | | |
|---|---|---|
| EP | 0040589 A2 | 11/1981 |
| WO | 2005/006017 A1 | 1/2005 |

OTHER PUBLICATIONS

A. La Rosa et al., "A Pixel Ionization Chamber Used as Beam Monitor at the Institut Curie-Centre de Protontherapie de Orsay (CPO)" Nuclear Instruments & Methods in Physics Research, Section A: Accelerators, Spectrometers, Detectors and Associated Equipment, Elsevier, Amsterdam, NL, vol. 565, No. 2, Sep. 15, 2006, pp. 833-840.

(Continued)

*Primary Examiner* — David Porta
*Assistant Examiner* — Carolyn Igyarto
(74) *Attorney, Agent, or Firm* — Fitch, Even, Tabin & Flannery, LLP (57) ABSTRACT

A device and method for on line dosimetry monitoring of a hadron beam generated from a source of radiation and delivered to a target, the device comprising a plurality of support plates arranged in parallel in a face-to-face relation, separated from each other by gas filled gaps and perpendicularly to the central axis of said hadron beam, and forming a plurality of ionization chambers, each support plate having on a first side one or more collecting electrodes and on a second side one or more high voltage electrode, arranged in such a way that each support plate has said first side substantially opposed to said second side of another support plate. Each support plate has an opening so as to form an inner cavity for allowing the undisturbed passage of a central portion of the hadron beam delivered to said target and a peripheral region for intercepting and measuring, by means of said plurality of ionization chambers, a peripheral portion of said hadron beam.

8 Claims, 6 Drawing Sheets

(56) References Cited

U.S. PATENT DOCUMENTS 5,326,967 A     7/1994    Herrmann et al.
5,672,878 A     9/1997    Yao

OTHER PUBLICATIONS

Stanislav I. Potashev et al., "A Thin-Walled Air-Ionization Chamber for Proton Therapy" Nuclear Instruments & Methods in Physics Research, Section A: Accelerators, Spectrometers, Detectors and Associated Equipment, Elsevier, Amsterdam, NL, vol. 535, No. 1-2, Dec. 11, 2004, pp. 115-120.

E. Badura et al., "Control System for Cancer Therapy With a Heavy Ion Beam at GSI" IEEE Transcations on Nuclear Science, vol. 47, No. 2, Apr. 2000, pp. 170-173.

C. Brusasco et al., "Verification of 3D dose distributions in heavy-ion radiotherapy." Jpn. Soc. Ther. Radio!. Oncol., vol. 9, 1997, 8 pages.

International Preliminary Report on Patentability and Written Opinion, International Patent Application No. PCT/EP2008/053774, Oct. 6, 2009, 6 pages.

International Search Report, International Patent Application No. PCT/EP2008/053774, date of completion Jul. 3, 2008, 3 pages.

DEVICE AND METHOD FOR ONLINE QUALITY ASSURANCE IN HADRON THERAPY

CROSS REFERENCE TO RELATED APPLICATIONS

This application is a national phase application of International Application No. PCT/EP2008/053774, filed Mar. 29, 2008, designating the United States and claiming priority to European Patent Application No. 07105403.5, filed Mar. 30, 2007, both of which are incorporated by reference herein in their entirety.

TECHNICAL FIELD

The present invention relates to the field of Hadron Therapy, i.e. radiation therapy using strongly interacting particles. More particularly, the invention relates to a device and method for measuring the dose in dependence of the depth in a target volume, known as the "Bragg Peak". Furthermore, the invention relates to a device and method for measuring the Spread-Out Bragg Peak (SOBP) when the range is modulated.

DESCRIPTION OF RELATED ART

It is well known, nowadays, that hadrons (i.e. neutrons, protons, pions, ions such as carbon ions) have physical advantages with respect to X-rays or gamma rays in the radiotherapy fields. Protons of a given energy, i.e. forming a monoenergetic proton beam, have a certain range and do not penetrate beyond that range. Furthermore, they deposit their maximum value of radiation energy in the so-called Bragg Peak, which corresponds to the point of greatest penetration of the radiation in a target volume. Since, the Bragg peak position depends on the energy of the hadron beam, it is evident that by precisely controlling and modifying the energy one can place the Bragg Peak at a suited depth of a tumour so as to administer the greatest radiation energy to that point and spare, by contrast, healthy tissue surrounding said tumour. Moreover, by combining several monoenergetic proton beams of different energies (i.e. performing the range modulation) it is possible to extend the Bragg Peak in order to match the thickness of the tumour and irradiate the target with a uniform dose while controlling the dose load on surrounding healthy tissue and critical organs.

Evidently, special equipment, such as a modulation wheel, is needed to combine together hadrons of different energies. Furthermore, special equipment is also required to shape the hadron beam in such a way as to match, as much as possible, the shape, size and location of the tumour.

Quality assurance in radiotherapy generally consists of particular procedures needed to ascertain the consistency and the correctness of medical prescriptions. Such procedures normally relate to the prescribed dose to the target volume to be irradiated and the dose, which should be as minimal as possible, to healthy tissue. Such procedures also relate to minimal exposure of personnel to irradiation and adequate delivery monitoring. Quality assurance in hadron therapy requires even more stringent procedures with respect to the conventional radiotherapy. Practically, conventional radio therapy quality assurance procedures are no more sufficient in hadron therapy treatments which require, in particular, full control of beam intensity and energy. For that purpose, suitable dosimetry systems must be provided. Therefore, even if dosimetry in radiotherapy is broadly established, hadron therapy requires new dosimetry systems that should allow measurements of both the absorbed dose in a point as well as 2D and 3D dose distributions.

Such a dosimetry system should have as main features: high sensitivity, small dimensions, fast dynamic response, radiation hardness, no dependence on energy and dose-rate, tissue equivalence and linear dose response.

Typically a transmission ion chamber comprises a housing encapsulating an ionizable gas, e.g. air, wherein two spaced electrodes, i.e. the high voltage electrode and the collecting electrode, are arranged in parallel or in the form of coaxial cylinders and between which a voltage is applied to produce an electric field. Typically, the high voltage electrode is connected to a high voltage supply and the collecting electrode is grounded through a low impedance of a current-voltage converter. When ionizing radiation enters the chamber, some of the atoms or molecules of the gas become ionized, and a current flows between the electrodes. Ions or electrons ionized by the radiation are therefore liberated and attracted to the collecting electrode and this current is converted into voltage by the current-voltage converter, and then amplified by an amplifier to have a given signal on a display, so that this signal can be monitored as a dose. Examples of such an ionization chamber are described in documents U.S. Pat. Nos. 4,131,799, 5,326,967 or 5,041,730.

It is also known from U.S. Pat. No. 5,672,878 an ionization chamber which is suitable for monitoring both an electron or photon beam. This ionization chamber mainly comprises a housing having a primary beam passageway and an array of secondary beam cells adjacent to the primary beam passageway. The housing also contains a first array of beam measuring electrodes which provides outputs that are responsive to detection of the radiation intensity of a portion of the electron or photon beam. Also second beam measuring electrodes are contained in the housing in order to provide outputs responsive to the radiation intensity of a second portion of said beam. Nevertheless, this device is only suitable for monitoring geometric characteristics of the radiation beam such as direction and position. Moreover, this device is not capable of monitoring radiation characteristics during the delivery to a target.

Another transmission ion chamber system is described in the document EP0040589. This system is suitable for carrying out a method for measuring and correcting the symmetry and the centering of a radiation beam. This transmission system is located between a collimator and a target to be irradiated, and comprises: four inner collecting electrodes that are fully traversed by said beam; and outer electrodes that are traversed by the beam in a first part of their surfaces, while the remaining parts lie in the shadow of said collimator. However, this system is only suitable for controlling a divergent beam and correcting the centering and symmetry thereof. Further, similarly to the previous one, it is not capable of monitoring radiation characteristics during the delivery to a target.

A well known dosimetry system, suitable for performing fast routine 3D dose verification is the product Magic Cube developed by INFN and University of Torino ("Verification of 3D dose distributions in heavy-ion radiotherapy": C. Brusasco, R. Cirio, M. Donetti, F. Marchetto, C. Peroni, D. Schardt, B. Voss. J. Jpn. Soc. Ther. Radiol. Oncol. 9 (1997), suppl. 2, p. 59). It consists of a sandwich of twelve 25 cm×25 cm parallel ionization chamber plates interleaved with tissue equivalent slabs of adjustable thickness. Each ionization chamber is defined by two plates of 0.1 mm thick vetronite (electrodes) wherein the conductivity is ensured by a 35 μm copper film. The cathode of this product is a continuous conductor, while the anode is splitted into 4 mm wide strips. The gap between two adjacent strips is 0.1 mm thick and it is filled with Argon (Ar) or Nitrogen (N). However, such a device is not capable of ensuring on line dose verification during the delivery to a target volume. It can only compare the prescribed and the delivered 3D dose distribution before the delivery of a hadron beam to a target.

There is therefore the need for a device and method for ensuring online verification and monitoring of a hadron beam during the delivery to a target volume without affecting the delivery of said beam.

In particular, the present invention aims to provide a device and a method which do not show the drawbacks of the state of the art.

The present invention aims to provide a device and method for measuring the dose in dependence of the depth in a target volume, known as the "Bragg Peak".

Furthermore, the present invention aims to provide a device and method for measuring the Spread-Out Bragg Peak (SOBP) when the range is modulated.

The present invention aims also to provide a device and method for measuring and monitoring the displacement or the asymmetry of a hadron beam.

Moreover, the present invention aims to provide such a dose monitoring device which is easy to manufacture and use, as well as easy to install and remove when required.

SUMMARY OF THE INVENTION

The present invention overcomes the shortcomings of the conventional art and may achieve other advantages not contemplated by conventional devices.

According to a first aspect of the invention, there is provided a device for on line dosimetry monitoring of a hadron beam generated from a source of radiation and delivered to a target, the device comprising a plurality of support plates arranged in parallel in a face-to-face relation, separated from each other by gas filled gaps and perpendicularly to the central axis of said hadron beam, and forming a plurality of ionization chambers, each support plate having on a first side one or more collecting electrodes and on a second side one or more high voltage electrode, arranged in such a way that each support plate has said first side substantially opposed to said second side of another support plate. Each support plate has an opening so as to form an inner cavity for allowing the undisturbed passage of a central portion of the hadron beam delivered to said target and a peripheral region for intercepting and measuring, by means of said plurality of ionization chambers, a peripheral portion of said hadron beam.

Advantageously, according to the first aspect of the invention, each support plate comprises an insulating material between said one or more collecting electrode and said at least one high voltage electrode.

More advantageously, each support plate comprises guard ring elements for reducing leakage currents in said one or more collecting electrode and in said at least high voltage electrode.

Preferably, said one or more collecting electrode and said at least one high voltage electrode are made of copper.

More preferably, said support plates are obtained by using the standard printed circuit board technique.

Advantageously, at least one support plate is turned by 90° with respect to the rest of said plurality of support plates, in order to check and measure the centering of said beam.

More advantageously, said at least one support plate is, in order, the first one to be intercepted by said hadron beam when the latter is being delivered to said target.

According to a second aspect of the present invention, there is provided a method for dosimetry verification of a hadron beam generated from a source of radiation and delivered to a target, the method comprising the steps of:
providing a device according the first aspect of the invention between said target and said source of radiation in such a way that the central axis of said device is superimposed to the central axis of said hadron beam;
delivering said hadron beam toward said target;
acquiring, in the peripheral region of said device, by means of said plurality of ionization chambers, measurements of the dose distribution of (or rather electrical signals from the peripheral portion of said hadron beam passing through said device; and simultaneously,
allowing the undisturbed passage of the central portion of said hadron beam passing through said inner cavity of said device.

More advantageously, the method further comprises the steps of:
comparing said measurements of the dose distribution with planned dose distribution for verifying the correctness of the delivery of said hadron beam;
measuring the range modulation and the SOBP uniformity of said hadron beam;

According to a third aspect, the invention also relates to the use of a device according to the first aspect or a method according to the second aspect of the invention for on line dosimetry monitoring of a hadron beam.

DETAILED DESCRIPTION OF THE INVENTION

Typically, a hadron therapy device mainly comprises an accelerator that accelerates hadrons, e.g. protons or carbon ions, in the form of a beam to a desired energy level and, through a beam transport line, delivers the hadron beam to a target. The last structure along the beam transport line and before said target comprises a nozzle which drives and shapes the hadron beam toward a specific target isocenter.

Figure 1:
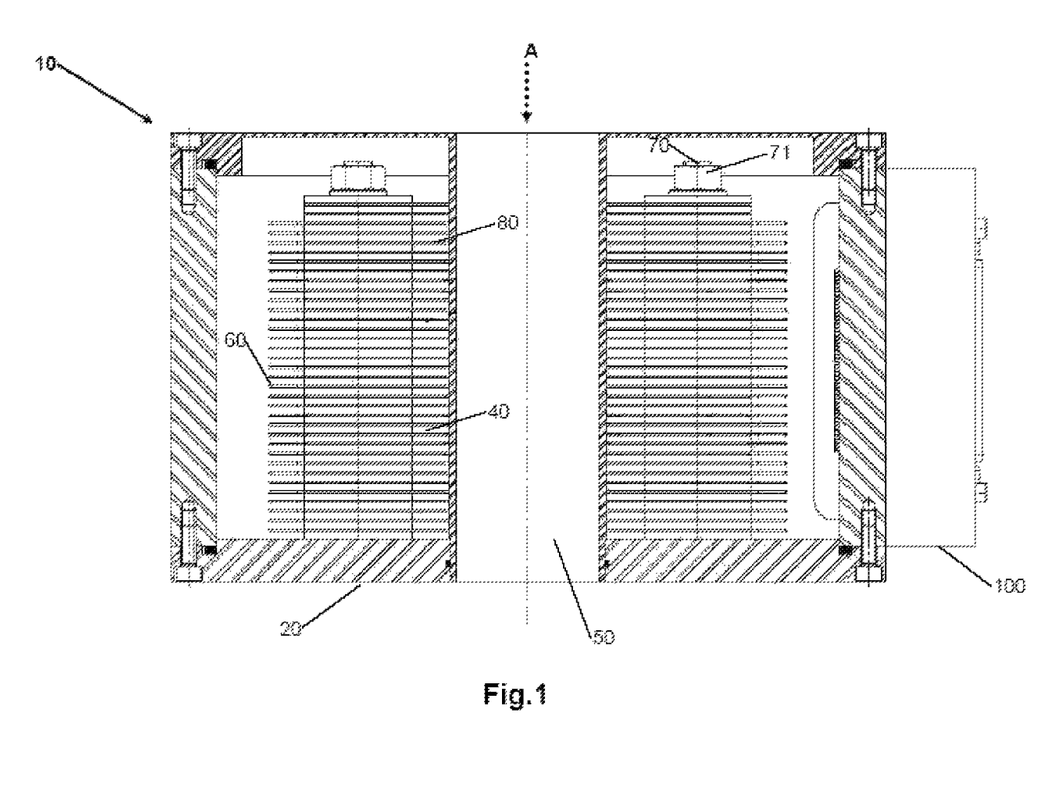
FIG. 1 is a sectional view of a device according to the invention.

FIG. 1 is a sectional view of a device according to a preferred embodiment of the invention. The device 10 is typically positioned between a source of radiation and a target, in such a Way that the central axis of the hadron beam corresponds to the central axis of the device 10. The device 10 comprises a housing 20 and a stack 30 of thirty-five ionization chambers stacked in parallel, preferably perpendicularly to the hadron beam direction, with gas therebetween and kept together by bolts 70 and nuts 71. Ionization chambers comprise successive opposed parallel support plates 80 that are positioned preferably perpendicular to the hadron beam direction and have a square shape with concentric rounded openings of 40 mm of diameter, in such a way as to form all along the length of the device 10 an inner region 50 and a peripheral region 60. The inner region is essentially hollow and cylindrically shaped and allows a portion of the hadron beam passing undisturbed through the device. The peripheral region 60 is radially outboard of the inner region 50 and intercepts another portion of the hadron beam. The total length along the direction of arrow A of the device 10 is approximately of 10 cm and provides measurements of the range modulation and SOBP uniformity.

Each support plate has on one side two collecting electrodes and on the other side a high voltage electrode. An ionization chamber of the stack 30 is realized by facing two support plates with 1.5 mm of gas 40 therebetween, in such a way that the side provided with two collecting electrodes of one support plate is opposed to the side provided with the high voltage electrode of the other support plate.

Figure 1A:
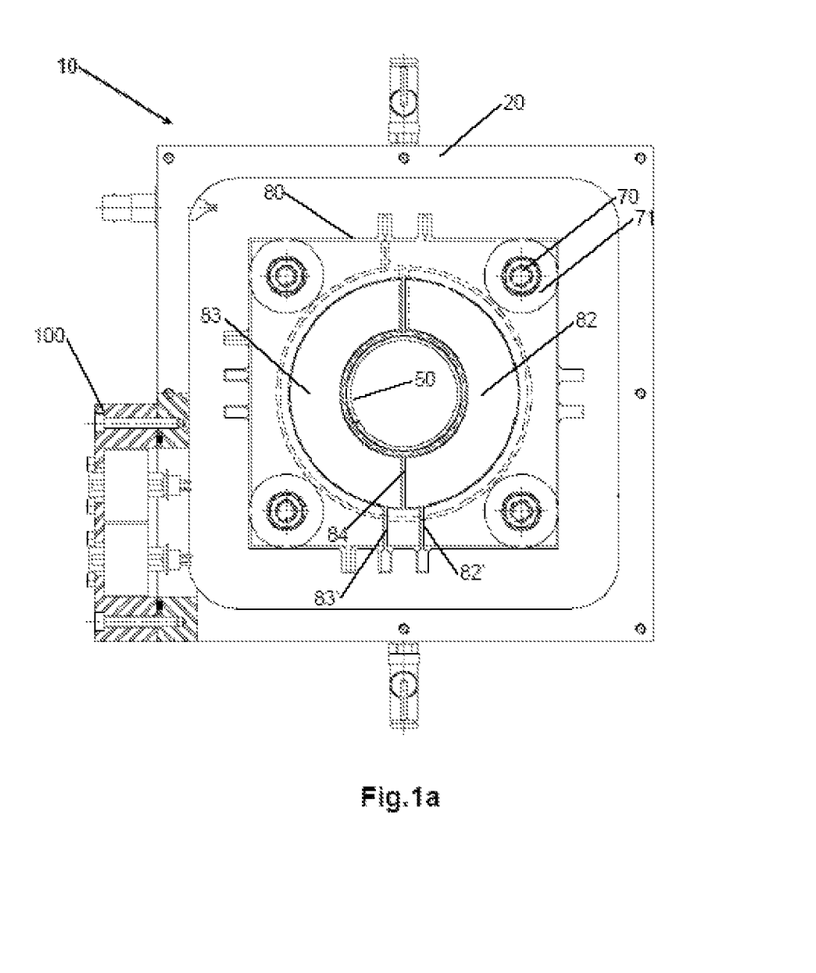
FIG. 1a is a view of the device of FIG. 1 along arrow A.

Support plate 80, as shown in FIG. 1*a*, comprises on one side two identical semi-annulus independent copper collecting electrodes 82, 83 which are connected by means of conductive traces 82' and 83' to the ground through acquisition electronics 100. The other side of the support plate 80 is provided with a high voltage copper electrode 87 which is connected to a high-voltage supply by means of conductive trace 87' (both shown by dashed lines). Outer region 85 and inner region 86 to the collecting electrodes 82 and 83, connected by traces through gaps 84, form a copper guard ring in order to reduce leakage currents in the collecting electrodes 82 and 83. Support plates are obtained by using the standard printed circuit board (hereinafter referred to as "PCB") technique, wherein a 0.5 mm thick FR4 plated board is covered by a 35 micron thick copper foil.

As water is the reference material for the treatment planning, it is needed to convert the total thickness of the device 10 to the corresponding water-equivalent thickness (WET).

Generally, the WET of a material i is defined as:

$$WET_i = d_i \rho_i \frac{\left(\frac{dE}{dx}\right)_i}{\left(\frac{dE}{dx}\right)_{water}}$$

Where:
  $d_i$ is the material thickness in cm;
  $\rho_i$ is the material density in g/cm$^3$;

$$\left(\frac{dE}{dx}\right)_i$$

is the proton (or another hadron) stopping power in the material in Mev*cm$^2$/g;

$$\left(\frac{dE}{dx}\right)_{water}$$

is the proton (or another hadron) stopping power in water in Mev*cm$^2$/g.

WET is normally used as a "common denominator" in order to characterize proton energy losses in various materials. The water equivalent of a degrader is the thickness of water that has the same energy loss. That is, water-equivalence is a common measure of proton (or another hadron) energy degradation in various materials. In particular for the present invention, according to a preferred embodiment, the value for the WET is 0.13 g/cm$^2$ for each ionization chamber.

This value is in fact calculated according to the above-discussed formula separately for each material (air, copper, printed board material) of an ionization chamber and results are summed up. Therefore, for example effective depth of 19-th channel is 19*0.13=2.47 g/cm$^2$, or 2.47 cm, since water density is 1 g/cm$^3$. In other words, WET allows to calculate the depth dose distribution in water (or in patient) knowing depth dose distribution measured by the device (1). Therefore, the device may provide measurements of the dose-distribution up to 4.55 cm in the target volume.

The housing 20 may be sealed, in order to provide a hermetical container filled of ionization gas.

Figure 5:
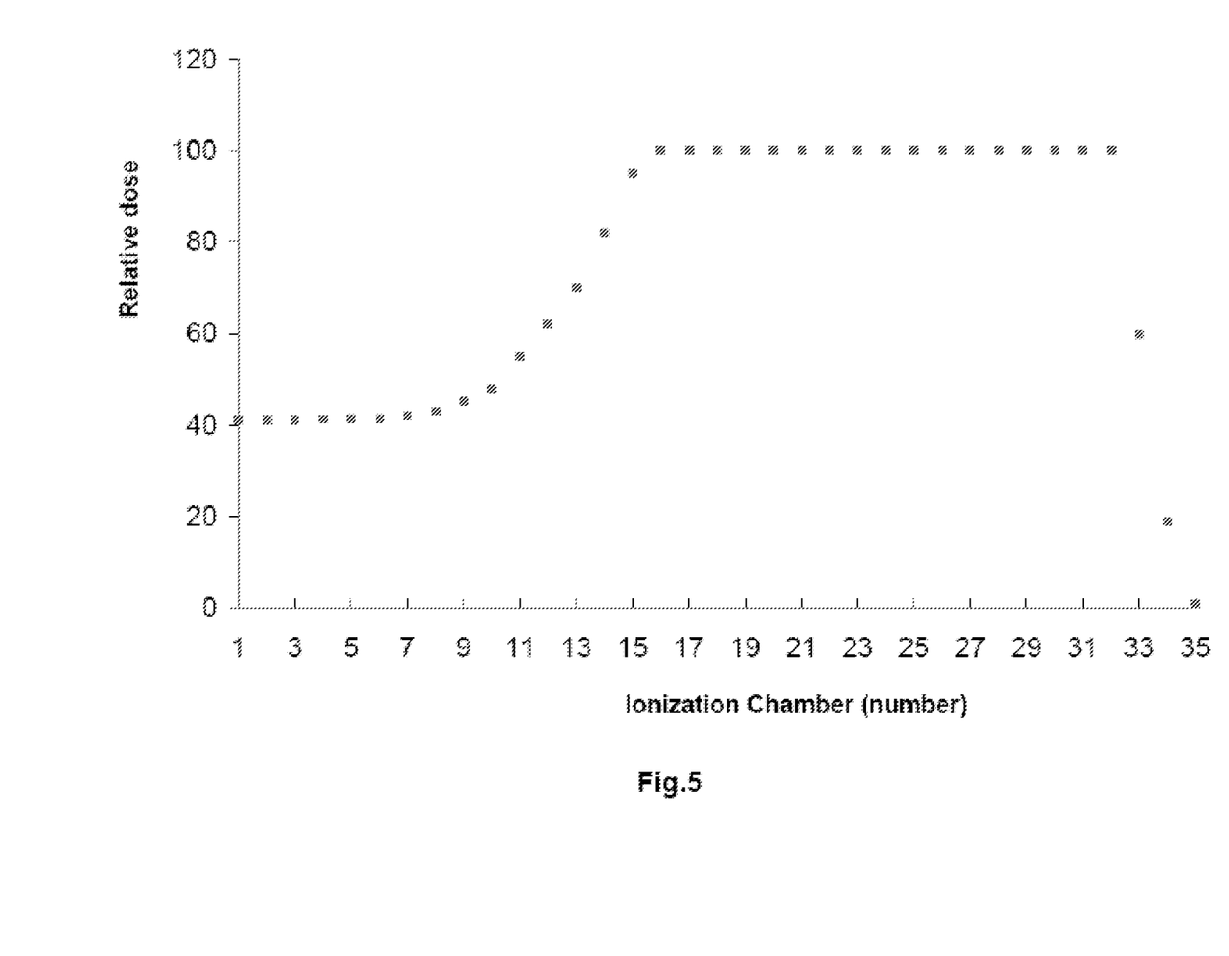
FIG. 5 is a graph showing the principle of depth-dose distributions measured by the device according to the invention.

When the device 10, according to the invention, is traversed by a hadron beam, the peripheral region 60 intercepts the peripheral portion of the beam and provides information on the hadron beam, by means of said stack 30 of ionization chambers. Simultaneous acquisition of the dose of a range modulated hadron beam is measured by each ionization chamber provides the histogram of FIG. 5, while the inner region 50 leaves undisturbed the passage of the central part of the beam to be delivered to the target. Each ionization chamber integrates the dose deposited during the measurement period.

The advantage of positioning the device 10 just upstream the patient is that its peripheral region it is capable of catching between 1.5% and 15% of the hadron beam, while the remaining portion of the beam passes undisturbed through the inner region 50 and is delivered to the target. In other words, this means, for example, that the device is crossed by 90-900 pA of said hadron beam having energy up to 70 MeV. As a consequence, with an air gap of 1.5 mm within the ionization chambers, the device may provide a read-out current between 4.5 nA and 45 nA.

Figure 2:
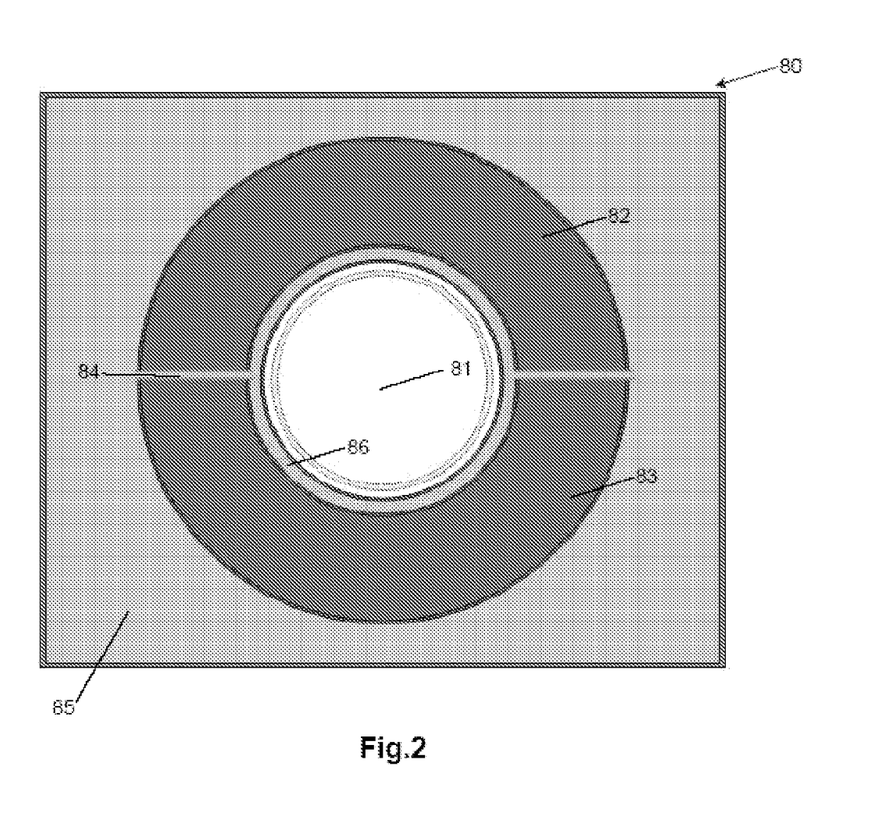
FIG. 2 and FIG. 3 are views of a support plate of the device of FIG. 1 along the direction of arrow A and in the reverse direction of arrow A respectively.

An acquisition electronics system is also provided and allows the device 10 to provide measurements of the hadron beam with a sampling rate comprised between 1 ms to 10 s, by means of 128 channels. In particular this acquisition system has the following functionality:
  It converts currents into digital values;
  It measures pressure and temperature;
  It controls the data exchange with the control system through an Ethernet protocol;
  It provide high voltage power supply to the measurement device;

FIG. 2 represents a view of a support plate of the device of FIG. 1 along the direction of arrow A. The support plate 80 has an opening 81 of 40 mm diameter and comprises two identical semi-annulus independent collecting electrodes 82 and 83, both providing redundant measurements. In fact, they should measure the same depth dose distribution and additionally provide information about beam asymmetry or displacement by comparing their reading values. Collecting electrodes 82, 83 are disposed in a common plane in spaced end-to-end relationship to form an annular disk having two gaps 84 and are connected to the ground and through acquisition electronics. Gaps 84 form a separation line between collecting electrodes 82, 83 which is perpendicular to hadron beam direction. Gaps 84 can be orientated either up and down or right and left With respect to the support plate 80. Collecting electrodes 82, 83 provide information about possible shift of the hadron beam in the direction perpendicular to the separation line. The inner radius of each collecting electrode is 2.6 cm and the outer radius is 4.6 cm. Gaps 84, the region 85 radially outboard of and the region 86 radially inboard of the collecting electrodes 82, 83 form a copper guard ring that is suitable for confining the excitation current within a defined area and for eliminating errors due to lateral spread of current signal from the collecting electrodes 82 and 83. This guard ring is separated from collecting electrodes by an insulating material and intercepts leakage currents so that to let them flow to ground bypassing the collecting electrodes.

Figure 3:
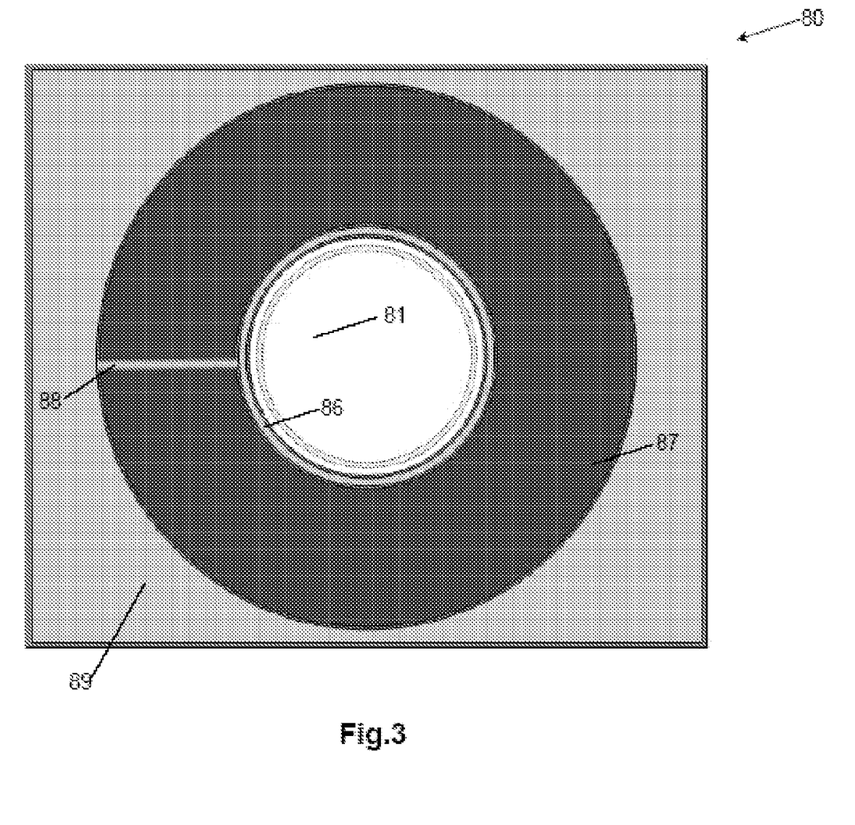

FIG. 3 represents a view of the support plate of the device of FIG. 2 along the reverse direction of arrow A. The support plate 80 comprises a high voltage electrode 87 which is traversed by a longitudinal gap 88 in order to provide, together with the region 89 radially outboard of and the region 86 radially inboard of the high voltage electrode 87, similarly as above-described, a guard ring. The high voltage electrode 87 is connected to a power supply that supplies a high voltage up to 300V, which is high enough to move ionized ions or electrons toward the collecting electrodes. The inner radius of the high voltage electrode is 2.6 cm, instead, the outer radius of the high voltage electrode exceed the outer radius of collecting electrodes and is approximately 5.1 cm.

Even if the above-described support plate has the collecting electrodes 82, 83 on the side seen along the direction of arrow A and the high voltage 87 on the side along the reverse direction of arrow A, it is evident for a man skilled in the art to easily conceive the inversed disposition of electrodes. It is also evident to fill the device 10, i.e. the ionization chambers of stack 30, with dry air or another gas.

Figure 4:
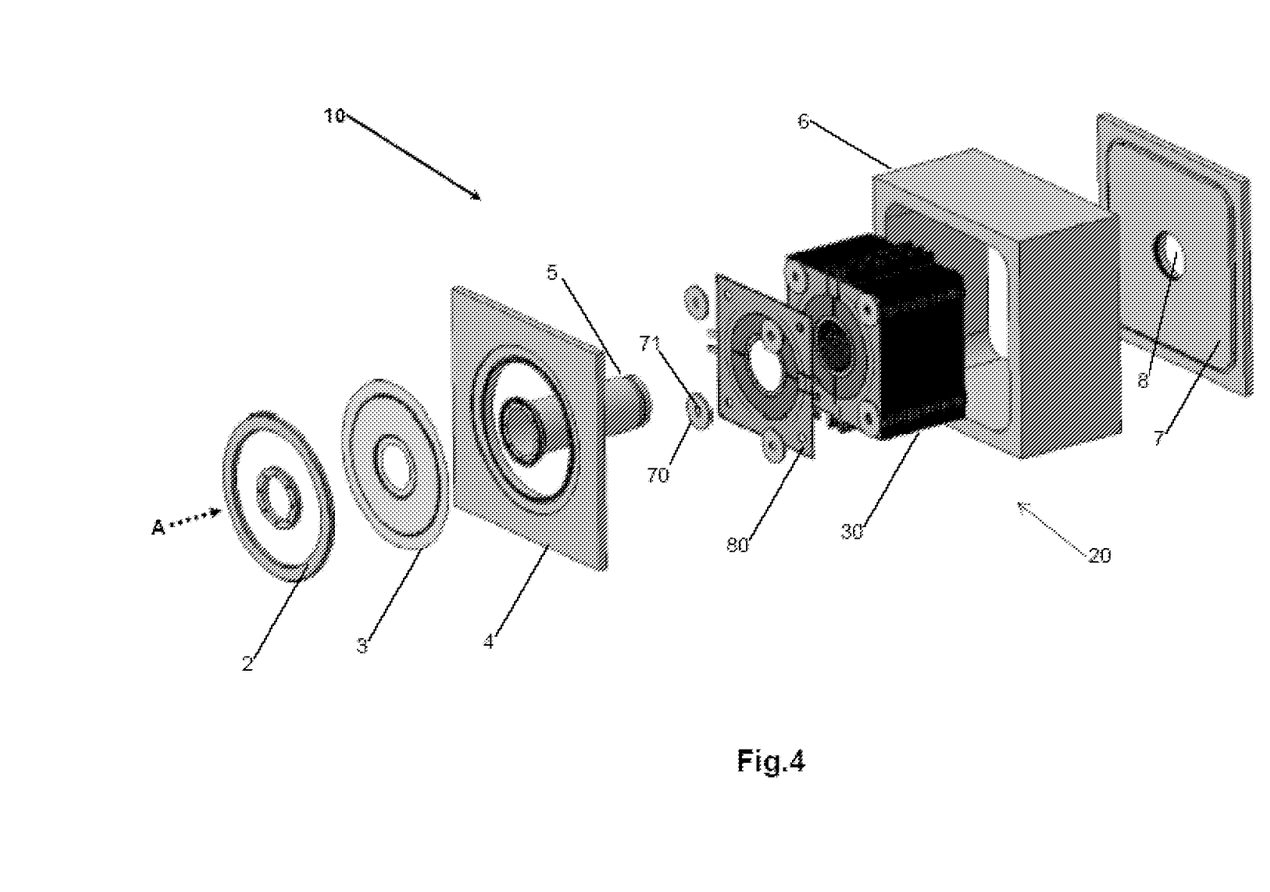
FIG. 4 is an exploded view of the device according to the invention.

FIG. 4 represents an exploded view of the device 10 according to a preferred embodiment of the invention. The device 10 comprises:
- a stack 30 of thirty-five ionization chambers that is perpendicular to the hadron beam passing therewithin;
- an aluminum sealed housing 20 comprised of: a sealing flange 2, a sealing window 3, an entry flange 4, bolts 70, nuts 71, a frame 6 and an exit flange 7 with a cavity 8. The sealed housing 20 provides electrical shielding and adequate faradization to the stack 30 of ionization chambers, as well as a hermetic support;
- a 40 mm aluminum inner pipe 5 going through the whole length of the device 10 for allowing the undisturbed passage of a portion of the hadron beam passing therewithin.

According to the invention, the first support plate, in order, to be traversed by incident hadron beam coming from said source of radiation, is turned by 90° with respect to the others. By turning this plate by 90° one can check and measure the shift of the hadron beam in the direction perpendicular to the separation line between collecting electrodes 82, 83.

In a variant of said preferred embodiment the inner pipe 5 can be made of plastic with aluminum paper wrapped around. In that case an electrical contact between the aluminum foil and the housing 20 is also provided.

In another variant of said preferred embodiment the inner pipe 5 is replaced by an aluminum thin foil and an aluminized mylar having a total thickness of 80 micron.

The device dimensions above-disclosed, e.g. the inner or outer radius of the high voltage electrode and collecting electrodes, diameter of opening 81, etc . . . , make the device 10 appropriate for real-time measurements for the treatment of eye cancers. However, it is evident for a man skilled in the art to easy conceive device dimensions suitable for the use of the device 10 in other radiotherapy applications.

One or more embodiments of the present invention have been described in detail with reference to the attached figures. It is evident that the invention is only limited by the claims, since the figures described are only schematic and therefore non-limiting. In the figures, the size of some of the elements may be exaggerated and not drawn on scale for illustrative purposes. The dimensions and the relative dimensions do not necessarily correspond to actual reductions to practice of the invention. Further, those skilled in the art can recognize numerous variations and modifications of this invention that are encompassed by its scope. Accordingly, the description of preferred embodiments should not be deemed to limit the scope of the present invention.

The description of preferred embodiments of the present invention is, in particular, referring to ophthalmologic applications, wherein is well known that a hadron beam with energy of 70 MeV is enough for the treatment of cancers of the eye. It is however evident for those skilled in the art that with the necessary adaptations other embodiments of the invention may be easily conceived for other applications, such as intracranial cancers, genitourinary cancers, gastrointestinal cancers, and so on. For example, one can easily achieve to add a tissue equivalent material (e.g. a plastic absorber) between ionization chambers of the device or to vary the number of ionization chamber in order to modify the WET and use a hadron beam with different energy values (235 MeV for example).

Furthermore, the terms first, second and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims may be used for descriptive purposes and not necessarily for describing relative positions. The terms so used are interchangeable under appropriate circumstances and the embodiments of the invention described herein can operate in other orientations than described or illustrated herein. For example "underneath" and "above" an element indicates being located at opposite sides of this element.

It is to be noticed that the term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

The invention claimed is:

1. A device for on line dosimetry monitoring of a hadron beam generated from a source of radiation and delivered to a target, the device comprising:
   a plurality of support plates arranged in parallel, separated from each other by gas filled gaps and positioned perpendicularly to the central axis of said hadron beam, and forming a plurality of ionization chambers,
   each support plate having on a first side one or more collecting electrodes and on a second side one or more voltage electrode, arranged in such a way that the first side of a support plate of said plurality of support plates is opposed to the second side of subsequent support plate,
   wherein each support plate has an opening so as to form an inner cavity for allowing an undisturbed passage of a central portion of the hadron beam delivered to said target and a peripheral region for intercepting and measuring, by means of said plurality of ionization chambers, a peripheral portion of said hadron beam.

2. The device according to claim 1, wherein each support plate comprises an insulating material between said one or more collecting electrode and said at least one voltage electrode.

3. The device according to claim 1, wherein each support plate comprises guard ring elements for reducing leakage currents in said one or more collecting electrode and in said at least one voltage electrode.

4. The device according to claim 1, wherein said one or more collecting electrode and said at least one voltage electrode are made of copper.

5. The device according to claim 1, wherein at least one further support plate is turned by 90° with respect to the rest of said plurality of support plates.

6. The device according to claim 5, wherein said at least one further support plate is, in order, the first one to be intercepted by said hadron beam when said hadron beam is being delivered to said target.

7. A method, for dosimetry verification of a hadron beam, generated from a source of radiation and delivered to a target, the method comprising the steps of:

providing a device for on line dosimetry monitoring of the hadron beam between said target and said source of radiation in such a way that the central axis of said device is superimposed to the central axis of said hadron beam;

delivering said hadron beam toward said target;

acquiring, in the peripheral region of said device, by means of a plurality of ionization chambers, measurements of dose distribution of the peripheral portion of said hadron beam passing through said device; and simultaneously allowing an undisturbed passage of the central portion of said hadron beam passing through an inner cavity of said device.

8. The method according to claim 7, further comprising the steps of:

comparing said measurements of the dose distribution with planned dose distribution for verifying the correctness of the delivery of said hadron beam; and measuring range modulation and Spread-Out Bragg Peak ("SOBP") uniformity of said hadron beam.

* * * * *